(12) United States Patent
Bates et al.

(10) Patent No.: US 6,743,252 B1
(45) Date of Patent: Jun. 1, 2004

(54) CANNULA STENT

(75) Inventors: Brian L. Bates, Bloomington, IN (US); Dale T. Berry, West Lafayette, IN (US); Neal E. Fearnot, West Lafayette, IN (US); Coy M. Herald, West Lafayette, IN (US); Palle M. Hansen, Bjaeverskov (DK); Jesper Thyregod, Roskilde (DK)

(73) Assignees: Cook Incorporated, Bloomington, IN (US); William Cook Europe ApS, Bjaeverskov (DK); MED Institute Incorporated, West Lafayette, IN (US)

( * ) Notice: Subject to any disclaimer, the term of this patent is extended or adjusted under 35 U.S.C. 154(b) by 0 days.

(21) Appl. No.: 09/464,895

(22) Filed: Dec. 16, 1999

Related U.S. Application Data (60) Provisional application No. 60/112,939, filed on Dec. 18, 1998.

(51) Int. Cl.[7] .................................................. A61F 2/06
(52) U.S. Cl. ...................................................... 623/1.15
(58) Field of Search ............................... 623/1.15, 1.16, 623/1.17, 23.7

(56) References Cited

U.S. PATENT DOCUMENTS

| | | | |
|---|---|---|---|
| 5,102,417 A | 4/1992 | Palmaz | |
| 5,104,404 A | 4/1992 | Wolff | |
| 5,133,732 A | 7/1992 | Wiktor | |
| 5,135,536 A | 8/1992 | Hillstead | |
| 5,195,984 A | 3/1993 | Schatz | |
| 5,314,444 A | 5/1994 | Gianturco | |
| 5,421,955 A | 6/1995 | Lau et al. | |
| 5,514,154 A | 5/1996 | Lau et al. | |
| 5,569,295 A | 10/1996 | Lam | |
| 5,591,197 A | 1/1997 | Orth et al. | |
| 5,593,442 A | 1/1997 | Klein | |
| 5,632,771 A | 5/1997 | Boatman et al. | |
| 5,643,339 A | 7/1997 | Kavteladze et al. | |
| 5,649,952 A | 7/1997 | Lam | |
| 5,681,346 A | 10/1997 | Orth et al. | |
| 5,697,971 A | 12/1997 | Fischell et al. | |
| 5,707,386 A | 1/1998 | Schnepp-Pesch et al. | |
| 5,718,713 A | 2/1998 | Frantzen | |
| 5,725,572 A | * 3/1998 | Lam et al. | 623/1.15 |
| 5,728,158 A | 3/1998 | Lau et al. | |
| 5,735,893 A | * 4/1998 | Lau et al. | 623/1.15 |
| 5,755,776 A | 5/1998 | Al-Saadon | |
| 5,759,192 A | 6/1998 | Saunders | |

(List continued on next page.)

FOREIGN PATENT DOCUMENTS

| | | | |
|---|---|---|---|
| WO | 9732544 | 9/1997 | |
| WO | 9851238 | 11/1998 | |
| WO | 9902105 | 1/1999 | |
| WO | 9915108 | 4/1999 | |
| WO | 9916387 | 4/1999 | |
| WO | WO 03/030786 A2 * | 4/2003 | 623/1.15 |

Primary Examiner—David H. Willse
Assistant Examiner—Suzette J. Jackson
(74) Attorney, Agent, or Firm—Richard J. Godlewski (57) ABSTRACT

A stent (10) formed from cannula and having flexible segments (11) and high hoop strength segments (12) alternating therealong. Axial tie bars (21,22) interconnect the segments; minimal length reduction would occur upon expansion. In the high hoop strength segment (12), struts (16) are initially parallel in the unexpanded strut condition, while in the flexible segment (11), struts (14) extend from a respective bight (15) to converge at distal ends when unexpanded. In one embodiment, certain adjacent struts (16) of the hoop segment are spaced apart by a large gap (20) while others are spaced apart by a small gap (18). In another embodiment all the struts (16) of the hoop segment are spaced apart uniformly from each other (or from an axial tie bar) by a small gap (23), resulting in minimizing the occurrence of fatigue of high-stress sites upon expansion/contraction cycles from continuous pulsatile events.

17 Claims, 8 Drawing Sheets

U.S. PATENT DOCUMENTS

| | | |
|---|---|---|
| 5,776,161 A | 7/1998 | Globerman |
| 5,817,152 A | 10/1998 | Birdsall et al. |
| 5,827,321 A | 10/1998 | Roubin et al. |
| 5,843,164 A | 12/1998 | Frantzen et al. |
| 5,843,175 A | 12/1998 | Frantzen |
| 5,853,419 A | 12/1998 | Imran |
| 5,855,600 A | 1/1999 | Alt |
| 5,860,999 A | 1/1999 | Schnepp-Pesch et al. |
| 5,868,782 A | 2/1999 | Frantzen |
| 5,938,697 A * | 8/1999 | Killion et al. ............. 623/1.15 |
| 6,013,091 A * | 1/2000 | Ley et al. .................. 623/1.15 |
| 6,106,548 A * | 8/2000 | Roubin et al. ............. 623/1.15 |
| 6,129,755 A * | 10/2000 | Mathis et al. .............. 623/1.15 |
| 6,132,461 A * | 10/2000 | Thompson ................. 623/1.15 |
| 6,190,406 B1 * | 2/2001 | Duerig et al. ............. 623/1.15 |
| 6,475,233 B2 * | 11/2002 | Trozera ..................... 623/1.15 |
| 6,540,774 B1 * | 4/2003 | Cox .......................... 623/1.15 |
| 6,638,300 B1 * | 10/2003 | Frantzen ................... 623/1.15 |
| 2003/0088310 A1 * | 5/2003 | Hansen et al. ............. 623/1.16 |

\* cited by examiner

FIG. 9

CANNULA STENT

CROSS-REFERENCE TO RELATED APPLICATION

This application claims priority of provisional application Serial No. 60/112,939 filed Dec. 18, 1998.

TECHNICAL FIELD

This invention relates generally to medical devices and in particular to a stent made from cannula.

BACKGROUND OF THE INVENTION

Stents of both the balloon expandable and the self-expanding type are known that have been cut from metal cannula and expanded for placement, for example, in the vessels of a patient. In a number of designs, the stent can be comprised of first and second segments, one of which exhibits radial strength greater than that of the other. The lesser radial strength segment is then formed to have lateral flexibility greater than that of the first segment. This combination of segments provides a stent having both good radial strength as well as lateral flexibility.

One known stent is disclosed in U.S. patent application Ser. No. 09/160,122 filed Sep. 24, 1998 and assigned to the assignee hereof. The stent is fabricated from cannula and is defined by one or more longitudinal segments of laterally interconnected closed cells. Each closed cell is defined laterally by a pair of longitudinal struts that are interconnected at each end by a circumferentially adjustable member that deform to permit circumferential expansion while the length of the cell is maintained by the longitudinal struts. Adjacent ones of the longitudinal segments are joined by flexible interconnection segments that permit the stent to bend laterally and tat are comprised of curvilinear struts that form a series of serpentine bends that distribute lateral bending forces while only allowing a slight overall shortening of the stent. A short strut interconnects a longitudinal segment and an adjacent interconnection segment.

Other cannula stents are known from U.S. Pat. No. 5,421,955; U.S. Pat. No. 5,102,417; and U.S. Pat. No. 5,195,984. A wire frame stent having a number of stent segments is disclosed in U.S. Pat. No. 5,104,404.

However, a problem associated with certain multiple segment stents is that relatively high tensile strains are produced therein that cause areas of metal fatigue. As a result, after these stents have been subjected to pulsatile expansion and contraction due to blood flow, the high tensile strain areas will eventually fracture. In addition, bending and torsional loads to which the stent is subjected when the patient changes physical position, can also cause metal fatigue and subsequent fracture. By way of example, these multiple segment stents have various peripheral vessel applications such as in the carotid of the patient. In addition, these peripheral stents can be subjected to external forces such as the patient having external pressure applied to a vessel and causing its collapse or deformation.

It is desired to provide a stent from cannula, that includes segments of high radial strength alternating with segments of lesser radial strength but greater flexibility.

It is further desired to provide a stent that is especially useful in applications wherein it is subjected to pulsatile expansion and contraction due to blood flow, such as in arterial applications and particularly the aorta and the carotid artery.

SUMMARY OF THE INVENTION

The foregoing problems are solved and the technical advances achieved in the illustrative cannula stent of the present invention, wherein the stent has segments of high flexibility alternating with segments of high radial or hoop strength. The flexible segments have a serpentine configuration that loops back and forth upon itself, with struts projecting in spaced apart pairs from respective bights and then in the unexpanded stent condition, converging at distal ends that each join to other bights to connect with adjacent strut pairs, thus eventually forming a circumferential band. The hoop segments also have a serpentine configuration but have struts that in the unexpanded stent condition are parallel projecting in pairs from respective bights, and also join bights at distal ends to connect with adjacent strut pairs, with axial tie bars positioned between certain ones thereof that join to bights of strut pairs of the adjacent segment, to interconnect the hoop segment with flexible segments at least at one end of the hoop segment.

In a first embodiment, the hoop segments of the stent have a small gap between most pairs of adjacent parallel struts when the stent is unexpanded; certain pairs of adjacent parallel struts have a relatively large gap therebetween; the axial tie bars are each positioned in certain ones of the large gaps but with only small gaps between itself and the parallel struts along both sides thereof.

In a second embodiment of the present invention, the stent has hoop segments with uniformly spaced struts to provide a radial strength or hoop strength greater than that of the flexible segments of prior art stents. Advantageously, the struts in the flexible segments of the stent are orientated and spaced so as to provide tensile strains less than those in the higher radial or hoop strength segment. Furthermore, this uniformly spaced strut segment has axial interconnecting bars that remain in a longitudinal configuration during expansion and compression and eliminate twisting and deformation thereof as with conventional non-uniformly spaced struts. The uniform spacing of the struts significantly and advantageously reduces the high tensile strain areas and provides a stent with a superior fatigue resistance and life.

BRIEF DESCRIPTION OF THE DRAWINGS

Embodiments of the present invention will now be described by way of example with reference to the accompanying drawing, in which.

DETAILED DESCRIPTION

Figure 1:
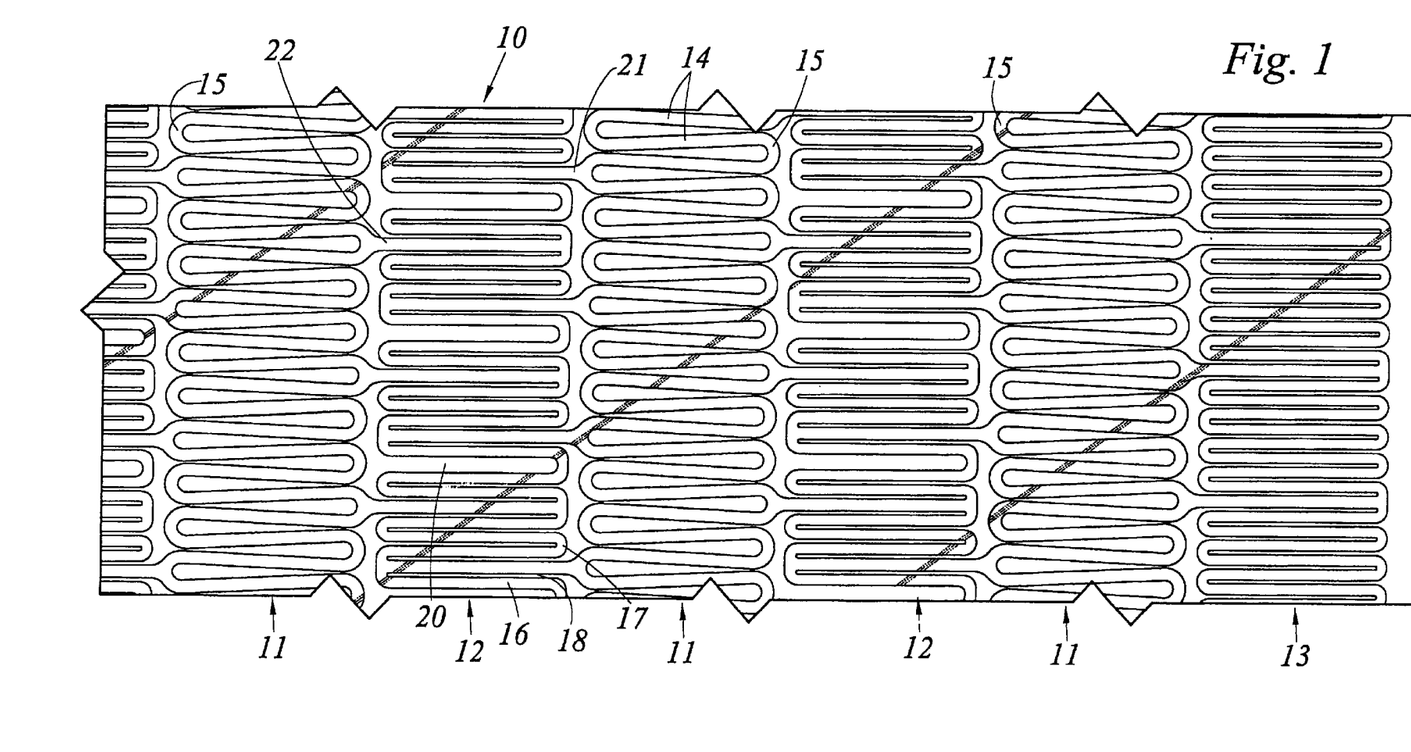
FIG. 1 depicts a flat view of the stent of the present invention cut from a cylindrical piece of cannula.

FIG. 1 depicts a flat view of stent 10 cut from a cylindrical piece of cannula. The stent includes a plurality of flexible interconnection segments 11 and higher hoop or radial strength cell segments 12, with end cell segment 13 preferably having high hoop strength. By way of example, the cannula can be comprised of Series 303 or 304 stainless steel that has applications for balloon expandable stents. In another application, the cannula can be formed of a nickel titanium alloy such as nitinol which can be employed for self-expanding stents. These nickel titanium self-expanding stents normally employ the superelastic properties of nitinol. By way of example, the stent is cut from a piece of cannula when in its compressed condition and then is expanded to its larger diameter expanded state. In the larger diameter expanded state, the nitinol material is heat set so that the stent retains its expanded configuration. The stent is then collapsed and introduced into a guiding catheter for deployment at the placement site.

As depicted, the flexible segments 11 are comprised of a serpentine configuration that loops back and forth upon itself with spacing between the struts 14 that varies from one longitudinal end of the segment to the other. Struts 14 project in spaced apart pairs from respective bights 15 and then, in the unexpanded stent condition, converge at distal ends that each join to other bights 15 to connect with adjacent strut pairs, thus eventually forming a circumferential band.

The hoop segments 12 also have a serpentine configuration and are comprised of a series of longitudinal struts 16 that are radially positioned with spacing therebetween that can vary circumferentially. Each pair of adjacent struts 16 extends in parallel from a respective bight 17 and are closely spaced to define narrow gaps 18, or in parallel from a respective bight 19 more generously spaced apart to define large gaps 20. Distal ends of the struts 16 of each pair join to other bights of adjacent strut pairs. Axial tie bars 21 extend from certain bights 19 within large gaps 20 to the right to connect with bights 15 of the adjacent flexible segment 11 to the right leaving narrow gaps between the axial tie bar and the adjacent struts 16 that may be equal in width to narrow gaps 18; similarly, axial tie bars 22 extend from certain bights 19 within large gaps 20 to the left to connect with bights 15 of another adjacent flexible segment 11 disposed on the left of hoop segment 12.

Figure 2:
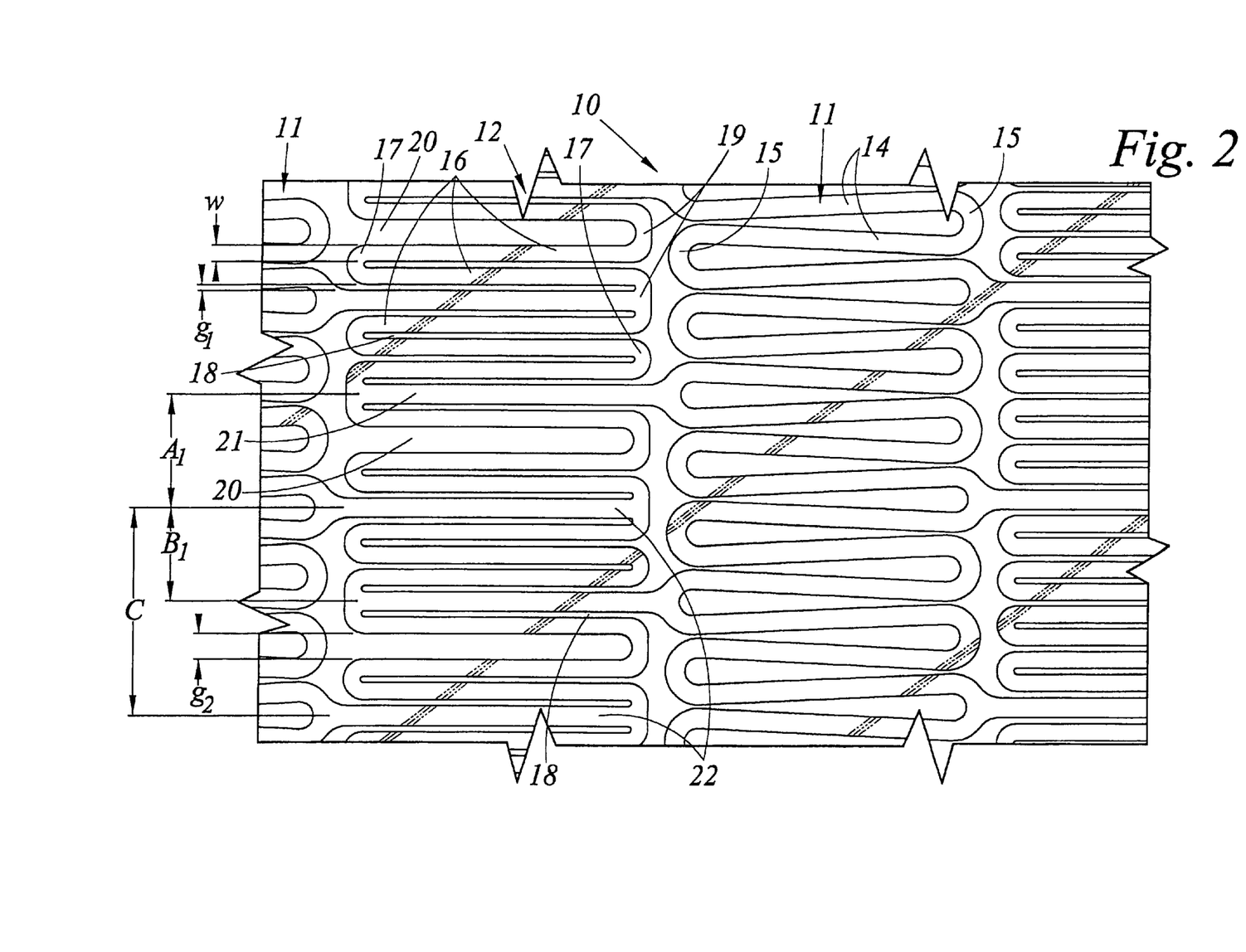
FIG. 2 depicts an enlarged view of the segments of the stent of FIG. 1.
Figure 3:
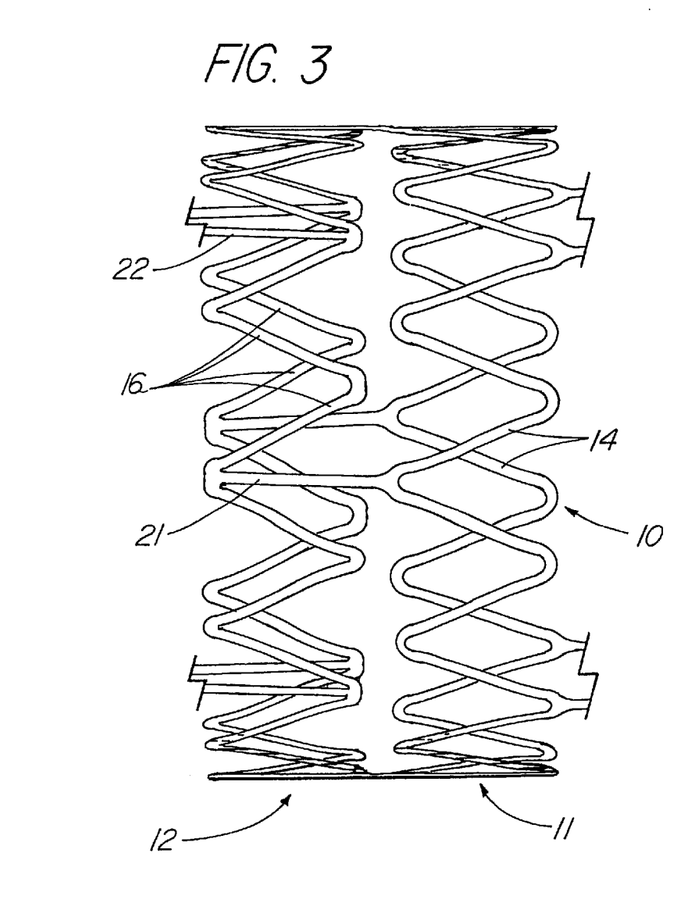
FIG. 3 depicts a side view of the stent of FIG. 1 when in an expanded state.

FIG. 2 depicts an enlarged view of segments 11 and 12 of stent 10 of FIG. 1. In particular, and by way of example, longitudinal struts 16 are approximately 0.142 mm in width (w), and narrow gaps 18 therebetween are approximately 0.026 mm wide ($g_1$). Large gap 20 between selected longitudinal struts 16 is approximately 0.194 mm wide ($g_2$). The length and width of the struts can be varied depending on the diameter of the overall stent. By way of further example, the starting cannula diameter of a stent is approximately 1.93 mm and may have a metal wall thickness of 0.007". In this configuration, the hoop cell segments are connected to the flexible segments by axial tie bars 21,22. With a configuration as described and shown, the expanded state of the stent is shown in FIG. 3 with non-uniform spacing between the struts of the hoop cell segment.

In FIG. 2, axial tie bars 21 are spaced circumferentially from each other approximately 1.512 mm (C). The axial tie bars 21 interconnecting hoop cell segment 12 with the adjacent flexible interconnection segment 11 extending to the right, are alternated circumferentially with respect to the axial tie bars 22 interconnecting it with the adjacent flexible interconnection segment 11 to the left. However, as shown, the distance $A_1$ between the midlines of axial tie bars 21,22 connecting right adjacent flexible interconnection segment 11 with left adjacent flexible interconnection segment 11 is 0.84 mm. This circumferential distance $A_1$ includes a large gap 20. Midline distance $B_1$ interconnecting adjacent flexible interconnection segments including substantially only narrow gaps 18 of minimal width, is 0.672 mm. As a result, distance $A_1$ is greater than distance $B_1$ with non-uniform spacing between circumferential segments. The total of distance $A_1$ and $B_1$ is approximately 1.512 mm.

Figure 4:
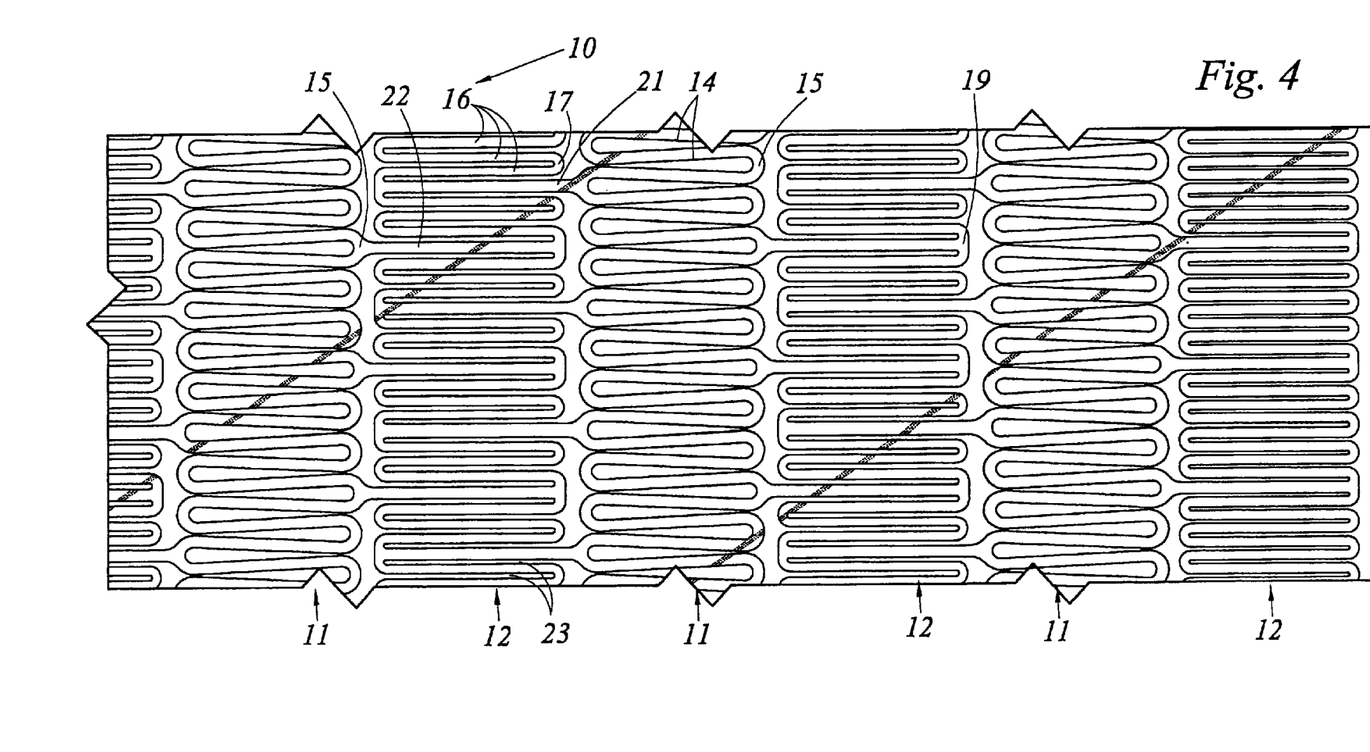
FIG. 4 depicts a flat view of alternative embodiment of the stent of the present invention cut from a cylindrical piece of cannula.

FIG. 4 depicts a flat view of an alternative embodiment of stent 10 of FIG. 1 cut from a cylindrical piece of cannula. The stent includes a plurality of flexible interconnection segments 11 and higher hoop or radial strength segments 12. As depicted, flexible segments are comprised of a serpentine configuration that loops back and forth upon itself with spacing between the struts 14 that varies from one longitudinal end of the segment to the other. Hoop cell segments 12 are comprised of a series of longitudinal struts 16 that are axially positioned with spacing therebetween that is uniform around the circumference thereof. Best seen in FIG. 5, hoop cell segment 12 has longitudinal struts 16 with medium gaps 23, for example, of 0.047 mm ($g_3$). The width of medium gap 23 is between the widths of narrow gap 18 and large gap 20 of the stent of FIG. 1. As a result, the tensile strains of the stent in FIG. 4 is significantly lower than the tensile strains of the stent in FIG. 1.

Figure 5:
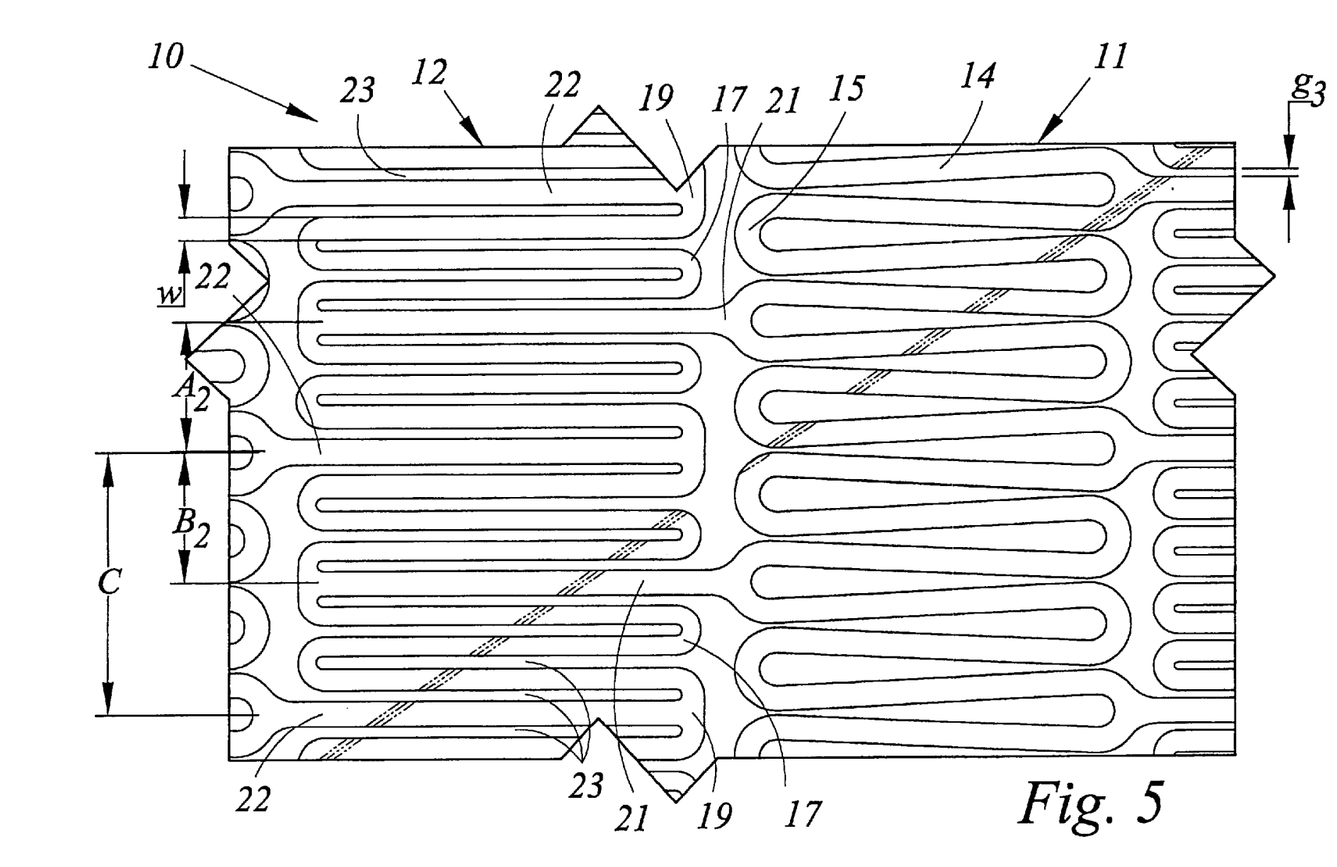
FIG. 5 depicts an enlarged view of the segments of the stent of FIG. 5, with uniformly spaced axial tie bars.

In FIG. 5, uniformly spaced gaps 23 provide for uniform radial expansion of the stent. Axial tie bars 21,22 are spaced circumferentially and uniformly from each other approximately 0.756 mm. The axial tie bars 21,22 interconnecting hoop cell segment 12 with adjacent flexible interconnection segments 11 are alternated circumferentially. However, as shown, the distance $A_2$ between the midline of axial tie bars 21,22 connecting right adjacent flexible interconnection segment 11 with left adjacent flexible interconnection segment 11 is 0.756 mm. This circumferential distance $A_2$ includes medium gaps 23 of approximately 0.047 mm. Midline distance $B_2$ interconnecting adjacent flexible interconnection segments including all uniform medium gaps 23 is again 0.756 mm. As a result, distance $A_2$ and $B_2$ is the same with uniform spacing between circumferential bars. The total of distance $A_2$ and $B_2$ is again approximately 1.512 mm.

Figure 6:
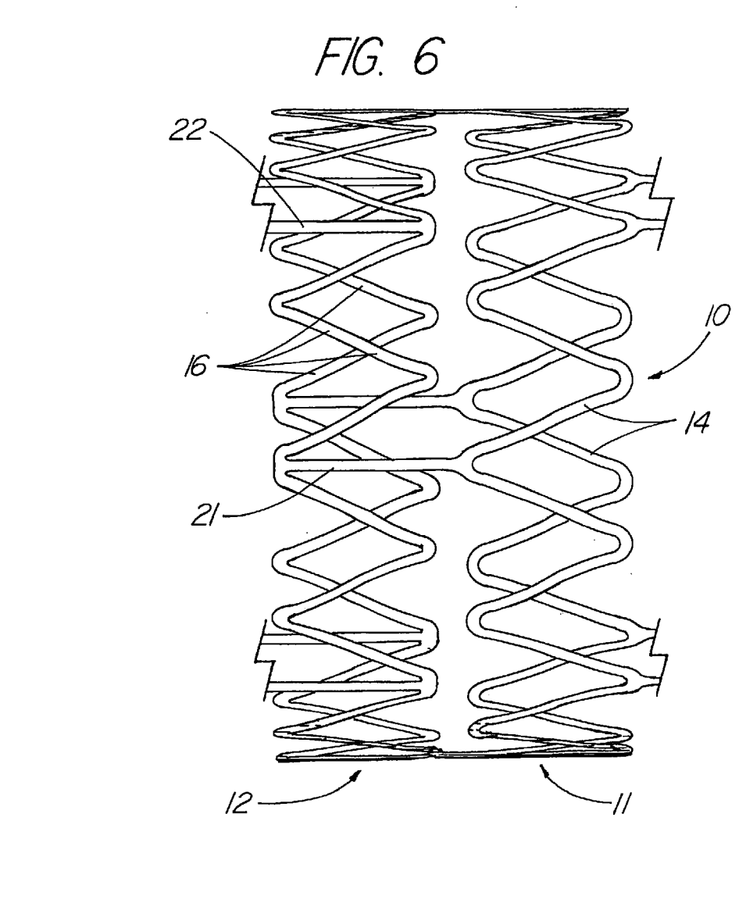
FIG. 6 depicts an expanded side view of the stent of FIG. 5 with the hoop cell segment and the flexible interconnection segment interconnected by axial tie bars.

FIG. 6 depicts an expanded side view of stent 10 of FIGS. 4 and 5 with the hoop cell segment 12 and flexible interconnection segment 11 interconnected by axial tie bars 21,22. The widths of all struts and tie bars in both FIGS. 3 and 6 is sufficiently small, that were the stent to be positioned at a vessel location which is the site of a branch, that flow into or from the branch would not be obstructed to a substantial extend by the stent. In comparison with axial tie bars 21,22 of FIG. 3, the axial tie bars 21,22 of FIG. 6 all remain in a longitudinal orientation. The axial tie bars 21,22 of the stent of FIG. 3 are twisted and are not all longitudinally oriented in the same direction and form various angles of inclination with respect to the longitudinal axis and cause a certain amount of twisting and flexing of the struts during expansion and contraction. This twisting of the axial tie bars provides for excessive fatigue and premature fracture. As previously pointed out, the non-uniform spacing between the longitudinal struts of hoop cell segment 12 of the stent of FIG. 1 causes the twisting of axial tie bars 21,22 and the undesired fatigue therein were the stent of FIG. 1 to be used in an arterial application wherein it would be continuously subjected to pulsatile activity.

Figure 7:
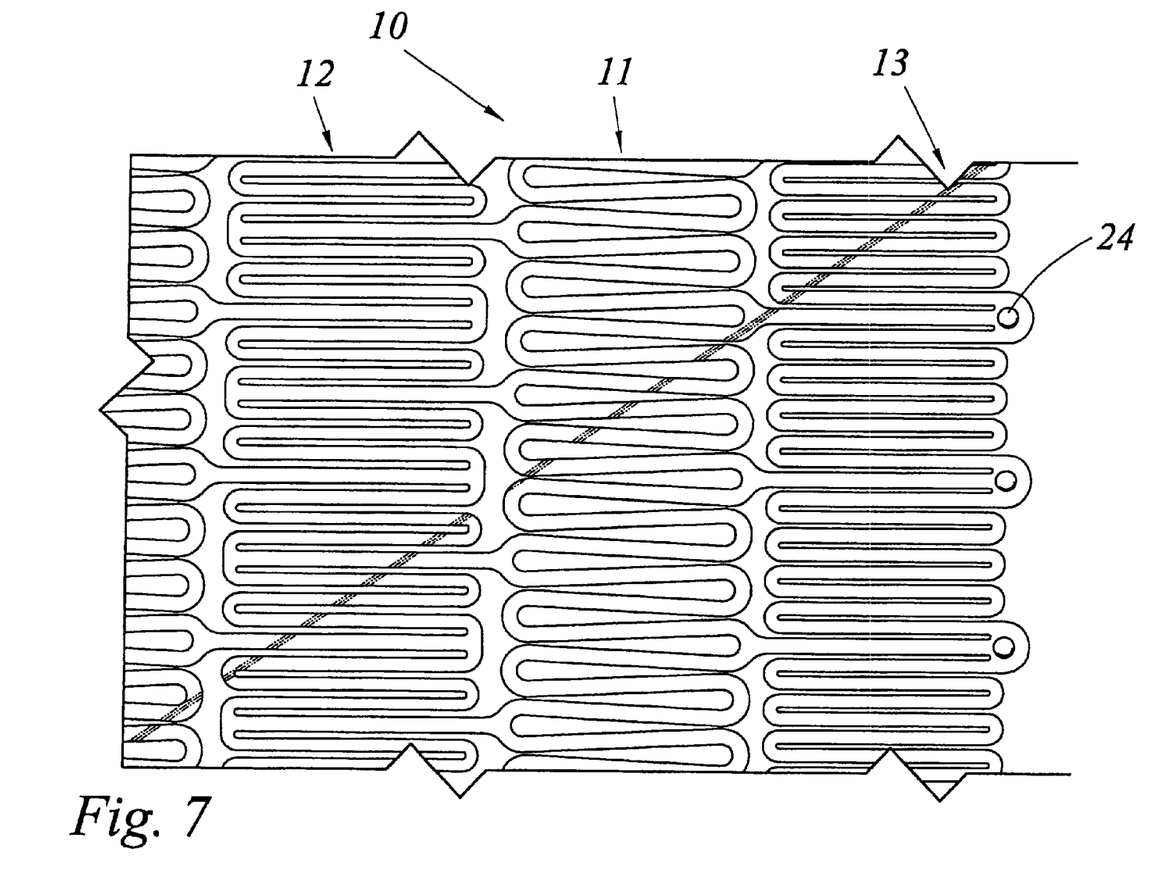
FIG. 7 depicts a flat view of the stent of respective FIGS. 4 and 5 with eyelets at the end cell of the stent.

FIG. 7 depicts the flat view of FIG. 4 with eyelets 24 at the end cell 13 of stent 10. By way of example, eyelets 24 are approximately 0.23 mm. These eyelets can be filled with various radiopaque materials such as gold sphere which are crushed into the aperture.

Figure 8:
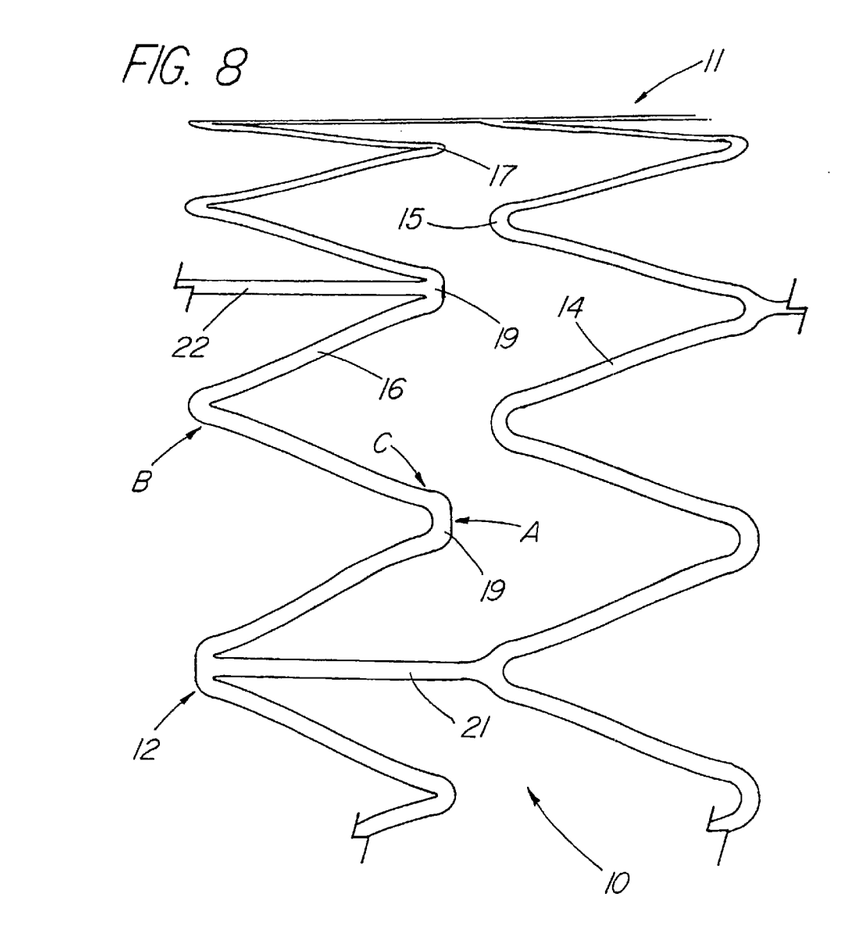
FIGS. 8 and 9 illustrate the stents of FIGS. 1 and 4 respectively in their expanded state.
Figure 9:
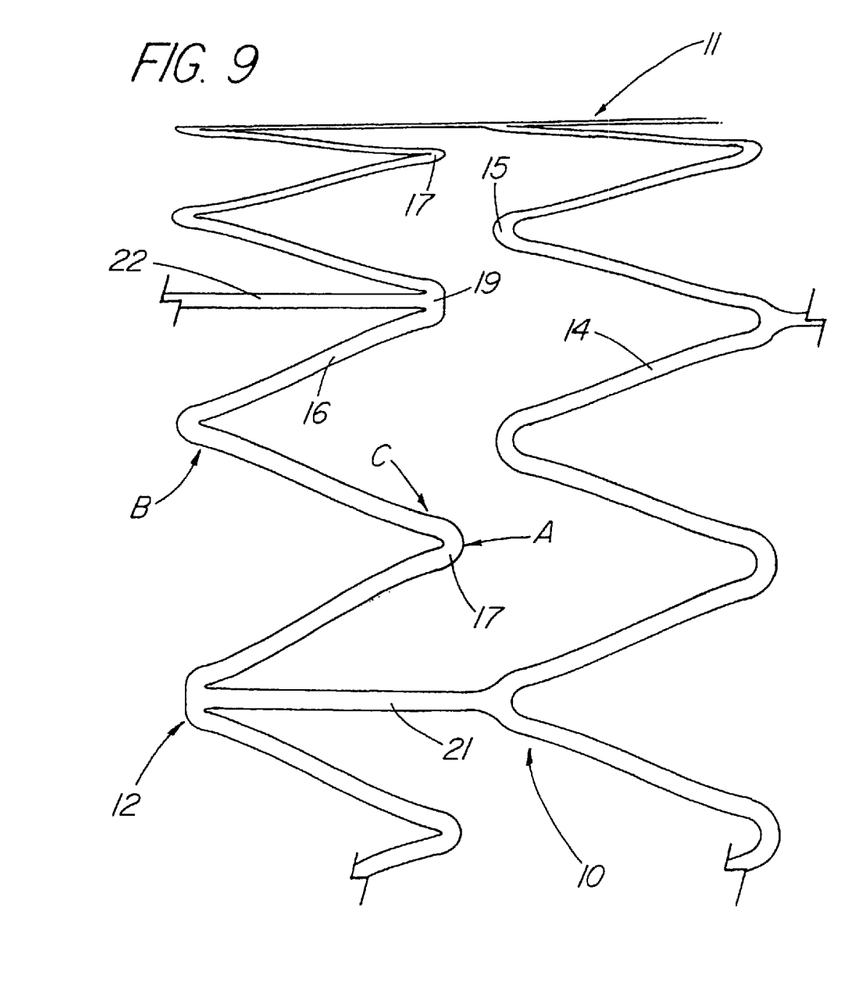

With reference to FIGS. 8 and 9, the stents of FIGS. 1 and 4 have each been expanded to a diameter of about 7.00 mm. Table I below provides a summary of the maximum principle tensile strains, taken at points A, B, and C of high radial strength segment 12, which are the sites of maximum strain.

TABLE I

| STENT DESIGN | STRAIN AT "A" | STRAIN AT "B" | STRAIN AT "C" |
| --- | --- | --- | --- |
| FIG. 8 | 0.0119 | 0.0100 | .00816 |
| FIG. 9 | 0.00665 | 0.00772 | 0.00772 |

By way of example, the maximum value for the stent of FIGS. 1 and 8 is about mm/mm while the maximum value for the stent of FIGS. 4 and 9 is 0.0078 about mm/mm, which is approximately 33% lower than that of the tensile strain of the stent of FIG. 1. Thus the stent of FIGS. 4 and 9 is appropriate for applications in vessels having substantial pulsatile events whereby the stent is subject to continuous expansion and contraction cycling.

In FIG. 1 to FIG. 7, it is seen that bights 15 of flexible segment 12 are semicircular, and that bights 17 of hoop segment 11 are also semicircular, but having a smaller radius. It may be seen in FIGS. 8 and 9 that bights 17 of hoop segment 12 are semicircular where not joined by an axial segment 21,22.

What is claimed is:

1. A cannula stent (10), comprising:
   at least one flexible segment (11) having a plurality of struts (14) extending in pairs from bights (15), the struts of a said pair converging toward each other at respective distal ends thereof when the stent is unexpanded to join respective bights (15) of adjacent strut pairs, continuously about the stent circumference;
   at least one hoop segment (12) having a plurality of struts (16) extending in parallel in pairs from bights (17,19) when the stent is unexpanded; and
   said at least one flexible segment (11) is joined to least one hoop segment (12) by axial tie bars (21,22) extending from certain ones of bights (15) of said flexible segment (11) to certain ones of said bights (19) of said hoop segment (12), with said axial tie bars (21,22) being disposed between paired adjacent ones of parallel struts (16) in said hoop segment (12).

2. The stent (10) as set forth in claim 1 wherein at least some of said parallel struts (16) of said at least one hoop segment (12) are spaced apart by a small gap (18) having a width of about one-half the width of a strut (16) and others are spaced apart by a large gap (20) having a width of about one-and-one-half the width of a strut with the struts extending from round joints with linear bights (19) having a minimally short length.

3. The stent (10) as set forth in claim 1 wherein paired adjacent ones of said parallel struts (16) of said at least one hoop segment (12) are spaced from each other by a medium gap (23) having a width about equal with the width of a strut with struts (16) extending from semicircular bights (17), or spaced from adjacent axial tie bars (21,22) therebetween by a medium gap (23) and extend from round joints with linear bights (19) having short length.

4. The stent (10) as set forth in claim 1 wherein an end segment (13) is a hoop segment.

5. The stent (10) as set forth in claim 1 wherein the stent is of shape memory alloy.

6. The stent (10) as set forth in claim 1 wherein the stent is of nitinol.

7. The stent (10) as set forth in claim 1 wherein the stent is of stainless steel.

8. The stent (10) as set forth in claim 1 wherein the radius of the semicircular bights of the flexible segment is larger than the radius of semicircular bights of the hoop segment.

9. The stent (10) as set forth in claim 1 wherein all bights (17) of the hoop segment that are not joined to an axial segment (21,22), are semicircular.

10. A cannula stent, comprising;
    at least one flexible segment having a plurality of struts extending in pairs from bights, the struts of a said pair converging toward each other at respective distal ends thereof when the stent is unexpanded to join respective bights of adjacent strut pairs, continuously about the stent circumference;
    at least one hoop segment having a plurality of struts extending in parallel in pairs from bights when the stent is unexpanded, wherein the radius of semicircular bights of the flexible segment is larger than the radius of semicircular bights of the hoop segment; and
    said at least one flexible segment is joined to least one hoop segment by axial tie bars extending from certain ones of bights of said flexible segment to certain ones of said bights of said hoop segment, with said axial tie bars being disposed between paired adjacent ones of parallel struts in said hoop segment.

11. The stent as set forth in claim 10 wherein at least some of said parallel struts of said at least one hoop segment are spaced apart by a small gap having a width of about one-half the width of a strut and others are spaced apart by a large gap having a width of about one-and-one-half the width of a strut with the struts extending from round joints with linear bights having a minimally short length.

12. The stent as set forth in claim 10 wherein paired adjacent ones of said parallel struts of said at least one hoop segment are spaced from each other by a medium gap having a width about equal with the width of a strut with struts extending from semicircular bights, or spaced from adjacent axial tie bars therebetween by a medium gap and extend from round joints with linear bights having short length.

13. The stent as set forth in claim 10 wherein an end segment is a hoop segment.

14. The stent as set forth in claim 10 wherein the stent is of shape memory alloy.

15. The stent as set forth in claim 10 wherein the sent is of nitinol.

16. The sent as set forth in claim 10 wherein the stent is of stainless steel.

17. The stent as set forth in claim 10 wherein all bights of the hoop segment that are not joined to an axial segment are semicircular.

\* \* \* \* \*